United States Patent

Biber et al.

(10) Patent No.: US 10,335,035 B2
(45) Date of Patent: Jul. 2, 2019

(54) SHIM COIL DEVICE AND A MAGNETIC RESONANCE COIL SYSTEM HAVING A SHIM COIL DEVICE

(71) Applicant: Siemens Aktiengesellschaft, Munich (DE)

(72) Inventors: Stephan Biber, Erlangen (DE); Ralf Ladebeck, Erlangen (DE); Kuan Jin Lee, Singapore (SG); Sebastian Martius, Forchheim (DE); Elisabeth Weiland, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 855 days.

(21) Appl. No.: 14/867,504

(22) Filed: Sep. 28, 2015

(65) Prior Publication Data

US 2016/0089029 A1    Mar. 31, 2016

(30) Foreign Application Priority Data

Sep. 29, 2014  (DE) .......................... 10 2014 219 682

(51) Int. Cl.
*G01R 33/3875* (2006.01)
*A61B 5/00* (2006.01)
*A61B 5/055* (2006.01)
*G01R 33/3415* (2006.01)

(52) U.S. Cl.
CPC .............. *A61B 5/004* (2013.01); *A61B 5/055* (2013.01); *A61B 5/4312* (2013.01); *G01R 33/3875* (2013.01); *A61B 5/0555* (2013.01); *A61B 5/708* (2013.01); *G01R 33/3415* (2013.01)

(58) Field of Classification Search
CPC .................................................. G01R 33/3875
See application file for complete search history.

(56) References Cited

U.S. PATENT DOCUMENTS

| 6,023,167 | A | 2/2000 | DeMeester et al. |
| 6,100,695 | A | 8/2000 | DeMeester et al. |
| 9,274,191 | B2 | 3/2016 | Biber |
| 9,279,871 | B2 | 3/2016 | Shen et al. |

(Continued)

FOREIGN PATENT DOCUMENTS

| DE | 10 2013 214 125 A1 | 4/2014 |
| WO | WO-94/29741 A1 | 12/1994 |

OTHER PUBLICATIONS

Salomir et al.: "A fast calculation method for magnetic field inhomogeneity due to an arbitrary distribution of bulk susceptibility"; published online in Wiley InterScience (www.interscience.wiley.com) DOI 10.1002/cmr.b.10083; (2003).

(Continued)

*Primary Examiner* — Tse W Chen
*Assistant Examiner* — Jason M Ip
(74) *Attorney, Agent, or Firm* — Schiff Hardin LLP (57) ABSTRACT

A shim coil device for compensating for basic magnetic field inhomogeneities during medical magnetic resonance imaging of a breast of a patient, said shim coil has a housing with a contact surface that configures to bear against a patient, and at least one shim coil element having a shim coil axis. The shim coil is arranged on the patient such that the at least one shim coil axis has an angle of inclination $\alpha$ to the contact surface and/or to a patient surface, where $\alpha$ is $\geq 45°$ and $\alpha$ is $\leq 135°$.

12 Claims, 4 Drawing Sheets

(56) References Cited

U.S. PATENT DOCUMENTS

| | | |
|---|---|---|
| 2003/0094947 A1 | 5/2003 | Akgun |
| 2012/0274326 A1* | 11/2012 | Lee .................... G01R 33/3415 |
| | | 324/318 |
| 2012/0323113 A1 | 12/2012 | Biber |
| 2013/0165768 A1 | 6/2013 | Biber |
| 2013/0193968 A1 | 8/2013 | Biber |
| 2013/0207655 A1 | 8/2013 | Biber |
| 2013/0274594 A1 | 10/2013 | Biber |
| 2015/0054510 A1 | 2/2015 | Biber et al. |

OTHER PUBLICATIONS

Schenck .: "The role of magnetic susceptibility in magnetic resonance imaging: MRI magnetic compatibility of the first and second kinds", Med. Phys. vol. 23, No. 6, pp. 815-850, (1996).

Lee et. al.: "Patient-to-Patient Variation of Susceptibility-Induced B0 Field in Bilateral Breast MRI", in: Journal of Magnetic Resonance, 2012, vol. 36, pp. 873-880 (2012).

Lee ; "Population Variability of Susceptibility-Induced B0 Field in Bilateral Breast MRI", pp. 1475, Proc. Intl .Mag. Reson. Med vol. 20 p. 1476 (2012).

Hancu , et. al.: "Field Shaping Arrays: A Means to Address Shading in High Field Breast MRI", 2012, in: Journal of Magnetic Resonance Imaging (2012).

Hancu et al.: "On Shimming Approaches in 3T Breast MRI", in: Magnetic Resonance in Medicine, No. 69, pp. 862-867, (2013).

Lee et al.: "B0 Shimming in 3 T Bilateral Breast Imaging with Local Shim Coils", Proc. Intl. Soc. Mag. Reson. Med. vol. 19 (2011).

Brow, "Fat Suppression Techniques" www.users.on.net/~spinupdownunder/papers/fatsup/fatweb.htm, (2013).

\* cited by examiner

SHIM COIL DEVICE AND A MAGNETIC RESONANCE COIL SYSTEM HAVING A SHIM COIL DEVICE

BACKGROUND OF THE INVENTION

Field of the Invention

The present invention concerns a shim coil device, in particular for compensating for field inhomogeneities in the basic magnetic field during medical magnetic resonance imaging of a breast of a patient, the shim coil device being of the type that has a housing with a contact surface that is configured for bearing against a patient, and at least one shim coil element having a shim coil axis.

Description of the Prior Art

Imaging in magnetic resonance tomography is based on the spins of atomic nuclei in a subject being initially aligned in a basic magnetic field. For many applications, the homogeneity of the basic magnetic field is critically important for image quality, as well as for spatial registration of the images.

Due to the anatomy of the human body and its magnetic properties, for example a spatial distribution of a magnetic susceptibility, basic magnetic field inhomogeneities are produced as soon as the patient is introduced into a portion of a basic magnetic field. In the case of female patients undergoing a breast examination in a magnetic resonance system, for example, said basic magnetic field inhomogeneities occur in areas that are located along a longitudinal extent of the patient in the thoracic wall situated below the breast. The magnetic resonance examination is carried out with the patient, in particular a female patient, in a face-down position. During the magnetic resonance imaging of the patient's breast, a deviation of the basic magnetic field can be so great that imaging techniques that are based on high basic magnetic field homogeneity, such as spectral fat saturation and/or EPI (echo planar imaging) and/or magnetic resonance spectroscopy for example, fail in this instance and/or image quality problems are caused. Furthermore, inhomogeneities of this type are in most cases spatially localized to such an extent that the pre-installed shim coil elements that are already contained in magnetic resonance systems, which are part of the gradient coil, are unable to correct such inhomogeneities.

SUMMARY OF THE INVENTION

An object of the present invention is to enable a simple and efficient compensation of inhomogeneities of the basic magnetic field, in particular during a breast examination.

This object is achieved in accordance with the invention by a shim coil device for compensating for basic magnetic field inhomogeneities during medical magnetic resonance imaging of a breast of a patient, wherein the shim coil device has a housing with a contact surface that is configured to bear against a patient, and at least one shim coil element having a shim coil axis.

In accordance with the invention that the shim coil device can be arranged on the patient such that the at least one shim coil axis has an angle of inclination $\alpha$ to the contact surface and/or to a patient surface, where $\alpha$ is $\geq 45°$ and $\alpha$ is $\leq 135°$. A simple and efficient compensation of a basic magnetic field inhomogeneity during a magnetic resonance examination of a breast can be achieved by this structure. In particular, an inhomogeneity of the basic magnetic field in the region of transition from the breast to the thorax of the patient can be partially or fully compensated by the shim coil device. As a result, confidence in the diagnostic validity of the acquired magnetic resonance images can also be increased, since a clear separation of different tissue types can be realized in the magnetic resonance images. Alternatively or in addition, a simple assignment of differently represented regions in the magnetic resonance images to different tissue types can also be achieved.

The at least one shim coil axis can have an angle of inclination $\alpha$ to the contact surface and/or to a patient surface, where $\alpha$ is $\geq 35°$ and $\alpha$ is $\leq 125°$. More advantageously, the at least one shim coil axis has in this case an angle of inclination $\alpha$ to the contact surface and/or to a patient surface, where $\alpha$ is $\geq 25°$ and $\alpha$ is $\leq 115°$. In this case the at least one shim coil axis particularly advantageously has an angle of inclination $\alpha$ to the contact surface and/or to a patient surface, where $\alpha$ is $\geq 15°$ and $\alpha$ is $\leq 105°$.

Preferably, the at least one shim coil axis has an angle of inclination $\alpha$ of $90°$ to the contact surface and/or to a patient surface. As used herein, an angle of inclination $\alpha$ of $90°$ in this context is an angle of $90°$ plus a tolerance range, where the tolerance range amounts to a maximum of $\pm 10°$, and a maximum of $\pm 5°$.

As used herein, a shim coil axis means an axis of the at least one shim coil element of the shim coil device that is aligned perpendicularly to a flow direction of the shim current flowing in the at least one shim coil element. Furthermore, a patient surface as used herein means a surface of the patient at which the shim coil device is in contact and/or bears against the patient and/or rests on the patient during the medical magnetic resonance imaging.

Alternatively or in addition, when the patient on whom the shim coil device is arranged is positioned inside the magnetic resonance scanner for examination, the at least one shim coil axis has an angle of inclination $\beta$ to the basic magnetic field direction in the magnetic resonance scanner, where $\beta$ is $\geq 45°$ and $\beta$ is $\leq 135°$. In this case, the at least one shim coil axis can have an angle of inclination $\beta$ to the basic magnetic field direction of the magnetic resonance device, where $\beta$ is $\geq 35°$ and $\beta$ is $\leq 125°$. More advantageously, the at least one shim coil axis in this case has an angle of inclination $\beta$ to the basic magnetic field direction of the magnetic resonance device, where $\beta$ is $\geq 25°$ and $\beta$ is $\leq 115°$. More advantageously, the at least one shim coil axis in this case has an angle of inclination $\beta$ to the basic magnetic field direction of the magnetic resonance device, where $\beta$ is $\geq 15°$ and $\beta$ is $\leq 105°$. Preferably, the at least one shim coil axis has an angle of inclination $\beta$ of $90°$ to the basic magnetic field direction of the magnetic resonance device. As used herein, the angle of inclination $\beta$ of $90°$ in this context is an angle of $90°$ plus a tolerance range, where the tolerance range amounts to a maximum of $\pm 10°$ and preferably to a maximum of $\pm 5°$. By this embodiment of the invention, it is possible to achieve a simple and efficient compensation of a basic magnetic field inhomogeneity during a magnetic resonance examination of a breast. In particular, an inhomogeneity of the basic magnetic field in a region of transition from the breast to a thorax of the patient can be at least partially compensated by the shim coil device. As a result, confidence in the diagnostic validity of the acquired magnetic resonance images can also be increased, since a clear separation of different tissue types can be realized in the magnetic resonance images. Alternatively or in addition, a simple assignment of differently represented regions in the magnetic resonance images to different tissue types can be achieved.

In another embodiment development of the invention, in a state of the shim coil device positioned on the patient, the at least one shim coil element is arranged such that a region of a patient that exerts a disruptive effect on the homogeneity of the basic magnetic field is covered to a maximum of 50%. In this way, an adverse influence on a breast examination due to the shim coil device, in particular due to a local shim magnetic field induced by shim currents, can be prevented. The shim coil device is preferably arranged on the patient during a breast examination such that the region to be examined, in particular the breast region of the patient, is not covered by the shim coil element, and also the region of the patient that exerts a disruptive effect on the homogeneity of the basic magnetic field is covered by the shim coil device, in particular by the at least one shim coil element, to a maximum of 50%. Preferably, however, the shim coil device is arranged on the patient for the purposes of a breast examination such that the shim coil device and the region of the patient that exerts a disruptive effect on the homogeneity of the basic magnetic field are arranged on the patient together on the same side of the breast of the patient, for example on a side facing toward the head or on a side facing toward the feet. For example, the at least one shim coil element can be arranged at a distance of preferably 2 cm to 15 cm from the breast of the patient. Advantageously, the at least one shim coil element covers the region of the patient that exerts a disruptive effect on the homogeneity of the basic magnetic field to a maximum of 40%. More advantageously, the at least one shim coil element covers the region of the patient that exerts a disruptive effect on the homogeneity of the basic magnetic field to a maximum of 30%. Even more advantageously, the at least one shim coil element covers the region of the patient that exerts a disruptive effect on the homogeneity of the basic magnetic field to a maximum of 20%, and particularly preferably to a maximum of 10%.

The at least one shim coil element can have a circular shape or an oval shape or in a rectangular shape or a square shape or a spiral shape. An advantageous compensation of basic magnetic field inhomogeneity during a magnetic resonance examination of a breast can also be achieved by such shapes.

In a further embodiment of the invention, the at least one shim coil element is arranged at a distance of 0 cm to 2 cm from the contact surface. Alternatively, the at least one shim coil element can be arranged at a distance from the contact surface that is equal to half the depth of a breast coil receiving zone of a breast coil device. By this structure, an ideal or optimal distance can be set between the at least one shim coil element and the patient, thereby enabling a particularly efficient compensation of basic magnetic field inhomogeneity to be achieved during a magnetic resonance examination of a breast.

In a further embodiment of the invention, the shim coil device can have multiple shim coil elements that, in a state of the shim coil device arranged on the patient, are situated sequentially in a direction that is aligned transversely with respect to the longitudinal extent of the patient. Alternatively or in addition, the shim coil device can have multiple shim coil elements that, in a state of the shim coil device arranged on the patient, are situated sequentially in the direction of the longitudinal extent of the patient. Alternatively or in addition, the shim coil device can have multiple shim coil elements that, in a state of the shim coil device arranged on the patient, are situated offset with respect to one another in a direction from the shim coil elements to the patient. Multiple shim coil elements in this context means two or more shim coil elements, more preferably two to a maximum of fifteen shim coil elements, more preferably two to a maximum of ten shim coil elements, and particularly preferably two to a maximum of five shim coil elements.

This embodiment of the invention having multiple shim coil elements makes it possible to take into account individual, patient-specific, magnetostatic conditions during the magnetic resonance imaging of the breast of the patient, because of the multiple shim coil elements. In this way an asymmetric embodiment of a breast region of the patient and/or an asymmetric positioning of organs, for example of the lung and/or of the heart, of the patient can be taken into account in the compensation of the basic magnetic field inhomogeneity during the magnetic resonance examination, and the individual shim coil elements can be tuned (adapted) and/or driven accordingly. In particular, different shim currents can flow through the individual shim coil elements in order to compensate for the basic magnetic field inhomogeneity during the magnetic resonance examination. At the same time the shim coil elements can be arranged offset with respect to one another in the direction of the longitudinal extent of the patient and/or in a direction transverse to the longitudinal extent of the patient.

In a further embodiment of the invention, the shim coil device can also have an operating controller, with which the individual shim coil elements can be driven separately from one another. In this way, individual, patient-specific, magnetostatic conditions can be taken into account particularly easily and selectively during the magnetic resonance imaging of the breast of the patient in the compensation of the basic magnetic field inhomogeneities. This enables the same shim coil device to be used at all times for different patients having different individual magnetostatic conditions, since an adjustment to the patient can be effected by activation of the individual shim coil elements and/or a setting of individual shim currents in the individual shim coil elements.

Furthermore, the invention encompasses a magnetic resonance coil system having a local breast coil device and a shim coil device, wherein the shim coil device has a housing with a contact surface that is configured to bear against a patient, and at least one shim coil element has a shim coil axis, and the shim coil device can be arranged on the patient in such a way that the at least one shim coil axis has an angle of inclination $\alpha$ to the contact surface and/or to a patient surface, where $\alpha$ is $\geq 45°$ and $\alpha$ is $\leq 135°$.

This coil system makes it possible to achieve a simple and efficient compensation of the basic magnetic field inhomogeneity during a magnetic resonance examination of a breast. In particular, inhomogeneity of the basic magnetic field in a region of transition from the breast to the thorax of the patient can be at least partially compensated by the shim coil device. As a result, confidence in the diagnostic validity of the acquired magnetic resonance images can also be increased, since a clear separation of different tissue types in the magnetic resonance images can be realized. Alternatively or in addition, a simple assignment of differently represented regions in the magnetic resonance images to different tissue types can be carried out.

The advantages of the magnetic resonance coil system according to the invention substantially correspond to the advantages of the shim coil device according to the invention as described above. Features, advantages or alternative embodiment variants cited in this connection apply equally to the other aspect of the invention.

The local breast coil device and the shim coil device can be arranged sequentially in the direction of the longitudinal extent of the patient. In this case, the shim coil device can be embodied independently or separately from the local breast coil device. Alternatively, the shim coil device can be integrated within the local breast coil device. Furthermore, the shim coil device can be arranged on the patient in the direction of the longitudinal extent on a side of the local breast coil device facing toward the head of the patient or in the direction of the longitudinal extent on a side of the local breast coil device facing toward the feet of the patient.

DESCRIPTION OF THE PREFERRED EMBODIMENTS

Figure 1:
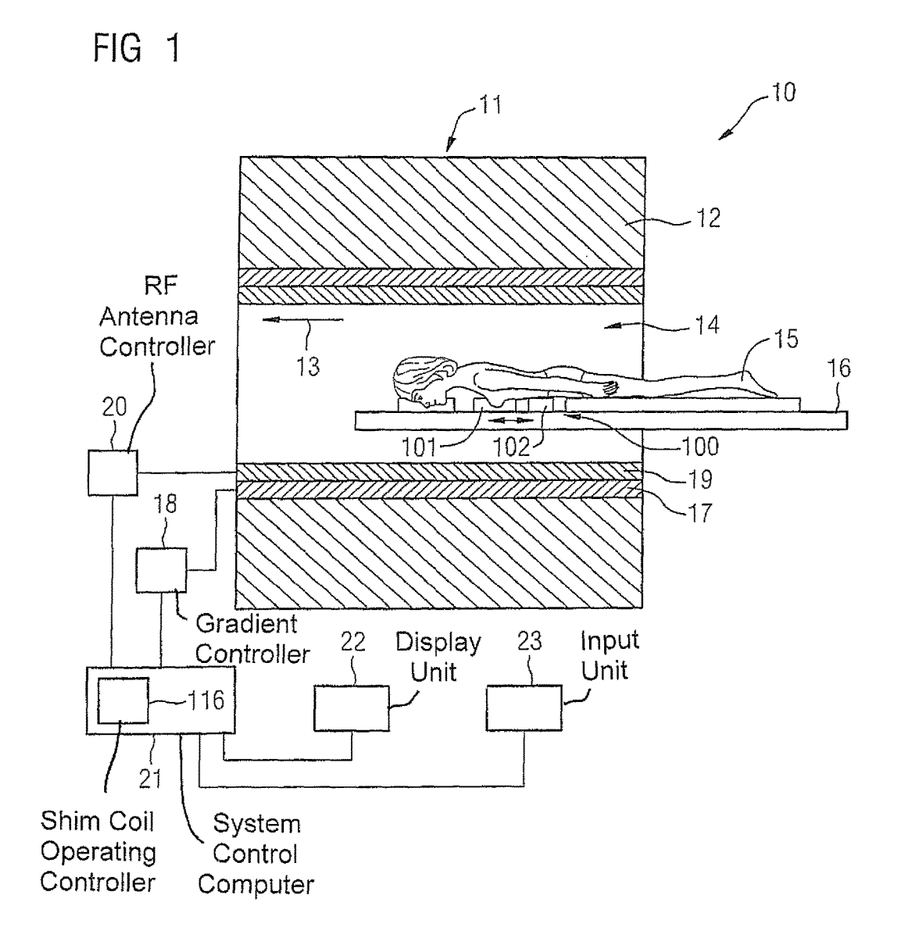
FIG. 1 schematically illustrates a medical imaging device having a magnetic resonance coil system.

A magnetic resonance apparatus 10 is shown schematically in FIG. 1. The magnetic resonance apparatus 10 comprises a scanner 11 having a superconducting basic field magnet 12 that generates a strong and constant basic magnetic field. The basic magnetic field has a basic magnetic field direction 13. The magnetic resonance scanner 11 has a patient receiving zone 14 for accommodating a patient 15. The patient receiving zone 14 in the present exemplary embodiment is embodied as a cylinder shape and is cylindrically enclosed by the scanner 11 in the circumferential direction. In principle, however, different embodiments of the patient receiving zone 14 are conceivable. The patient 15 can be introduced into the patient receiving zone 14 by a patient support device 16 of the magnetic resonance apparatus 10.

The scanner 11 also has a gradient coil unit 17 for generating magnetic field gradients that are used for spatial encoding during an imaging session. The gradient coil unit 17 is controlled by a gradient controller 18 of the magnetic resonance apparatus 10. The scanner 11 also has a radio-frequency antenna unit 19 for exciting nuclear spins in the patient so as to deviate from the polarization established by the basic magnetic field generated by the basic field magnet 12. The radio-frequency antenna unit 19 is controlled by a radio-frequency antenna controller 20 of the magnetic resonance apparatus 10 and radiates radio-frequency magnetic resonance sequences into an examination space that is substantially formed by the patient receiving zone 14 of the magnetic resonance apparatus 10.

The magnetic resonance apparatus 10 has a system control computer 21 for controlling the basic field magnet 12, the gradient controller 18 and the radio-frequency antenna controller 20. The system control computer 21 is responsible for the centralized control of the magnetic resonance apparatus 10, such as performing a predetermined imaging gradient echo sequence. In addition, the system control computer 21 has an evaluation processor (not shown) for evaluating medical image data acquired during the magnetic resonance examination. Control information such as imaging parameters, as well as reconstructed magnetic resonance images, can be displayed for medical operating personnel on a display unit 22, for example on at least one monitor, of the magnetic resonance apparatus 10. The magnetic resonance apparatus 10 also has an input unit 23 via which information and/or parameters can be entered by the medical operating personnel during a measurement procedure.

In addition, the magnetic resonance apparatus 10 has a local breast coil device 101 and a shim coil device 102 that are arranged to form a magnetic resonance coil system 100. For the purpose of a breast examination, the patient 15, in particular a female patient 15, is placed in a face-down position on the patient support device 16, a breast 24 of the patient 15 being arranged inside the local breast coil device 101, as can also be seen in FIGS. 1 and 2. For this purpose, the local breast coil device 101 is arranged directly on the patient support device 16. For the magnetic resonance imaging of the breast, an imaging zone 103, (a field of view) encompasses the breast 24 of the patient 15 as well as, at least partially, the region 25 of the patient 15 causing the disruption to the homogeneity of the basic magnetic field.

Figure 2:
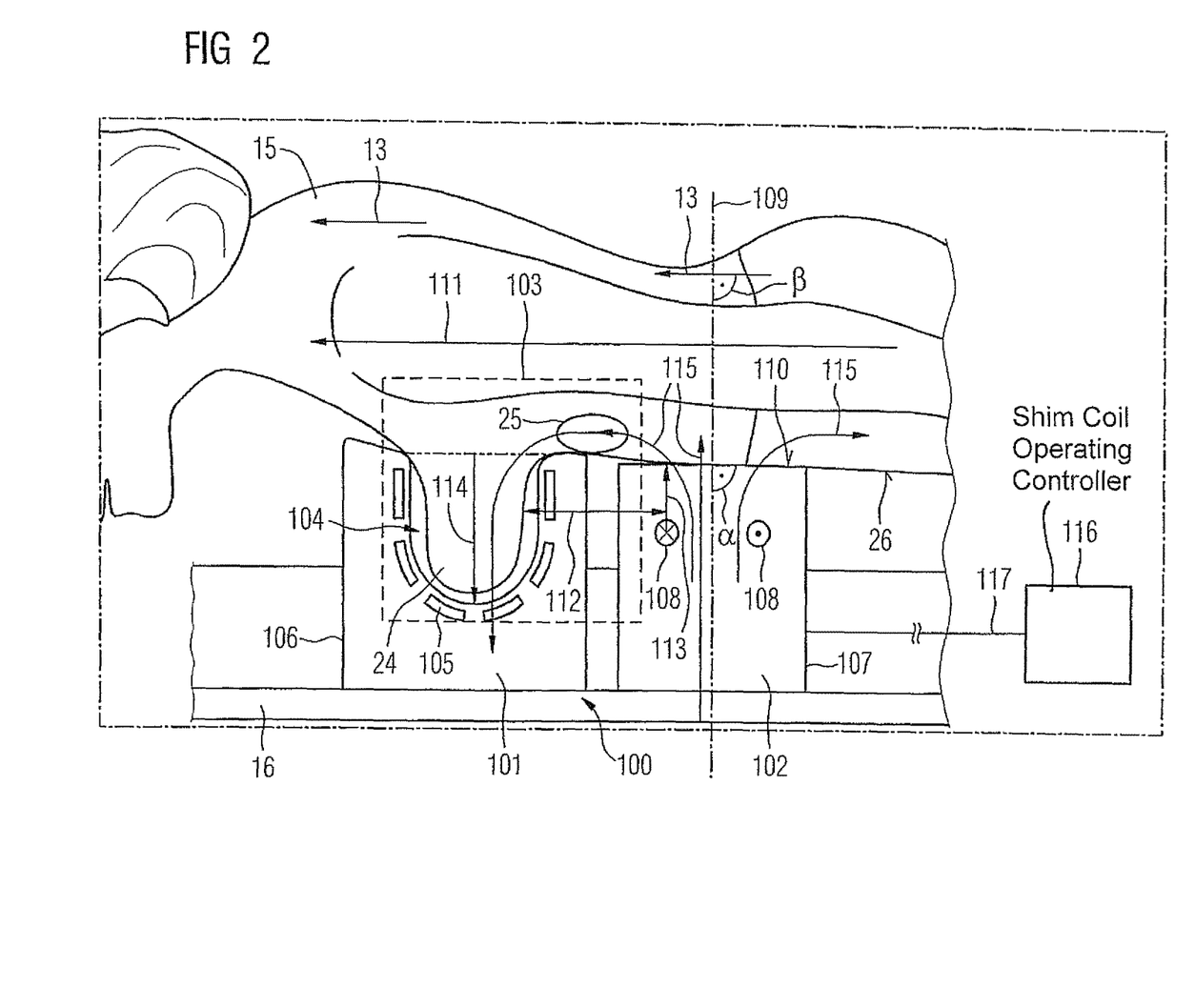
FIG. 2 schematically illustrates a magnetic resonance coil system having a shim coil device in a state positioned on the patient.

The breast coil device 101 has a breast coil receiving zone 104 that is configured to receive the breast 24 of the patient 15. Breast coil antennas 105 are arranged around the breast coil receiving zone 104. In a state of the magnetic resonance coil system 100 arranged on the patient support device 16, the local breast coil device 101 and the shim coil device 102 are situated sequentially on the patient support device 16 in the longitudinal extent of the patient support device 16. Furthermore, the local breast coil device 101 and the shim coil device 102 are formed by separate structural units, which have respective dedicated housings 106 and 107, which are embodied separately from one another.

In the shown exemplary embodiment, the shim coil device 102 is arranged in relation to the patient 15 toward the feet end with respect to the local breast coil device 101. In principle a different arrangement, such as an arrangement of the shim coil device 102 in relation to the patient 15 toward the head end with respect to the local breast coil device 101 is also possible.

The shim coil device 102 serves to compensate for basic magnetic field inhomogeneities during the acquisition of image data. These basic magnetic field inhomogeneities are caused by the patient 15. In particular, regions 25 in a transition from the breast 24 of the patient 15 to the thorax of the patient 15 lead to particularly strong basic magnetic field inhomogeneities, which have a detrimental impact on an acquisition of magnetic resonance image data of the breast region. This has a particularly negative effect with respect to the imaging of the breast 24, since usually the region 25 is also to be imaged, at least in part, in order to increase the level of confidence with regard to a diagnosis. The shim coil device 102 enables the basic magnetic field inhomogeneities to be compensated during the imaging. For the compensation of basic magnetic field inhomogeneities during the magnetic resonance imaging of the breast 24 of the patient 15, the shim coil device 102 is also arranged directly on the patient support device 16 and on the patient 15.

The shim coil device 102 has at least one shim coil element 108. In the shown exemplary embodiment in FIG. 2, the shim coil device 102 has a single shim coil element 108 having a shim coil axis 109. The shim coil axis 109 is aligned perpendicularly to the current direction of the shim current that flows through the shim coil element 108 during a compensation of basic magnetic field inhomogeneities. Furthermore, the shim coil device 102 has a housing unit 107 that shields (screens) the shim coil device 102 externally. The housing 107 has a contact surface 110 with which the shim coil device 102 bears against a patient 15 or on which the patient 15 rests for the purpose of a magnetic resonance examination of the breast 24. In a state arranged and/or positioned on the patient support device 16, the contact surface 110 of the shim coil device 102 is arranged on the shim coil device 102 on a side facing away from the patient support device 16.

The shim coil element 108 in FIG. 2 is arranged parallel to the contact surface 110. As a result, the shim coil axis 109 is arranged at an angle of inclination α to the contact surface 110, where the angle of inclination α in the present exemplary embodiment is equal to 90°. Due to the fact that in a state of the shim coil device 102 positioned on the patient 15, the shim coil device bears directly against the patient 15 at the contact surface 110, the shim coil axis 109 of the shim coil element 108 is accordingly also arranged at the angle of inclination α to a patient surface 26, where the angle of inclination α to the patient surface 26 is likewise equal to 90°. In this context an angle of inclination α of 90° is an angle of 90° plus a tolerance range, where the tolerance range amounts to a maximum of ±10°, and preferably to a maximum of ±5°. If the patient 15 is positioned on the patient support device 16 and if the latter is located together with the patient 15 inside the patient receiving zone 14, then the shim coil axis 109 is arranged at an angle of inclination β to the basic magnetic field direction, where the angle of inclination β in the present exemplary embodiment is equal to 90°. In this context an angle of inclination β of 90° is an angle of 90° plus a tolerance range, where the tolerance range amounts to a maximum of ±10° and preferably to a maximum of ±5°.

In a state arranged on the patient 15, the shim coil device 102 is arranged on the patient 15 such that the region 25 of the patient 15 that has a disruptive effect on the homogeneity of the basic magnetic field is covered to a maximum of 50% by the shim coil element 108. Advantageously, the at least one shim coil element 108 covers the region 25 of the patient 15 causing the disruption to the homogeneity of the basic magnetic field to a maximum of 40%. More advantageously, the at least one shim coil element 108 covers the region 25 of the patient 15 causing the disruption to the homogeneity of the basic magnetic field to a maximum of 30%. More advantageously, the at least one shim coil element 108 covers the region 25 of the patient 15 causing the disruption to the homogeneity of the basic magnetic field to a maximum of 20%, and preferably to a maximum of 10%.

The shim coil axis 109 of the shim coil element 108 extends through the patient 15 adjacent to the region 25 of the patient 15 causing the disruption to the homogeneity of the basic magnetic field. In the state in which the shim coil device 102 is arranged on the patient 15, the region 25 of the patient 15 causing the disruption to the homogeneity of the basic magnetic field is preferably located in the direction 111 of the longitudinal extent of the patient 15 between the breast 24 of the patient 15 and the shim coil device 102. The distance 112 of the shim coil element 108 from the breast of the patient 15 preferably amounts to between 2 cm and 15 cm.

The shim coil element 108 inside the shim coil device 102 is arranged at a distance 113 from the contact surface 110, the distance 113 having a value between 0 cm and 2 cm. Alternatively or in addition, the distance 113 of the shim coil element 108 from the contact surface 110 of the shim coil device 102 can be aligned with the local breast coil device 101. In this case the distance 113 can be equivalent to half the depth 114 of the breast coil receiving zone 104.

Figure 5:
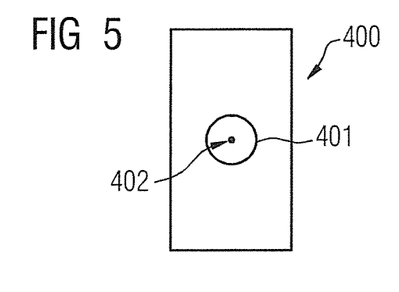
FIG. 5 schematically illustrates a further alternative exemplary embodiment of a shim coil device.

The shim coil element 108 in FIG. 2 can be embodied as a circular shape, as is also shown in FIG. 5. Alternatively, the shim coil element 108 can also be embodied as an oval shape (FIG. 8), or a rectangular shape (FIG. 6) or a square shape, or a spiral shape.

As can be seen in FIG. 2, a shim field 115 is generated by the shim coil element 108, the shim field being oriented substantially perpendicularly to the contact surface 110 in a region of the shim coil element 108. Influencing of the basic magnetic field by the shim field 115 is prevented as a result.

In the region 25 of the patient 15 causing the disruption to the homogeneity of the basic magnetic field, the shim field 115 extends perpendicularly or virtually perpendicularly to the shim coil axis 109 and consequently also parallel or virtually parallel to the basic magnetic field. As a result, in an operating state of the shim coil device 102, a basic magnetic field inhomogeneity in the region 25 of the patient 15 causing the disruption to the homogeneity of the basic magnetic field is at least partially compensated.

In the breast region of the patient 15, the shim field 115 again extends substantially perpendicularly to the basic magnetic field direction β and consequently does not influence the basic magnetic field. A region of the patient 15 that is located on a side of the shim coil device 101 facing away from the local breast coil device 101 is arranged outside of the imaging zone 103 for the magnetic resonance imaging, so in this case a possible influencing of the basic magnetic field by the shim field 115 can be discounted.

The shim coil device 102 additionally has an operating controller 116 configured to drive the shim coil element 108 in order to compensate for basic magnetic field inhomogeneities during medical magnetic resonance imaging. The operating controller 116 is arranged inside the system control computer 21 of the magnetic resonance apparatus 10, as can be seen in FIG. 1. The shim coil device 102 is connected to the operating controller 116 by a data transmission unit 117. The data transmission unit 117 can also be configured for performing a wireless and/or radio-based data transfer.

Figure 3:
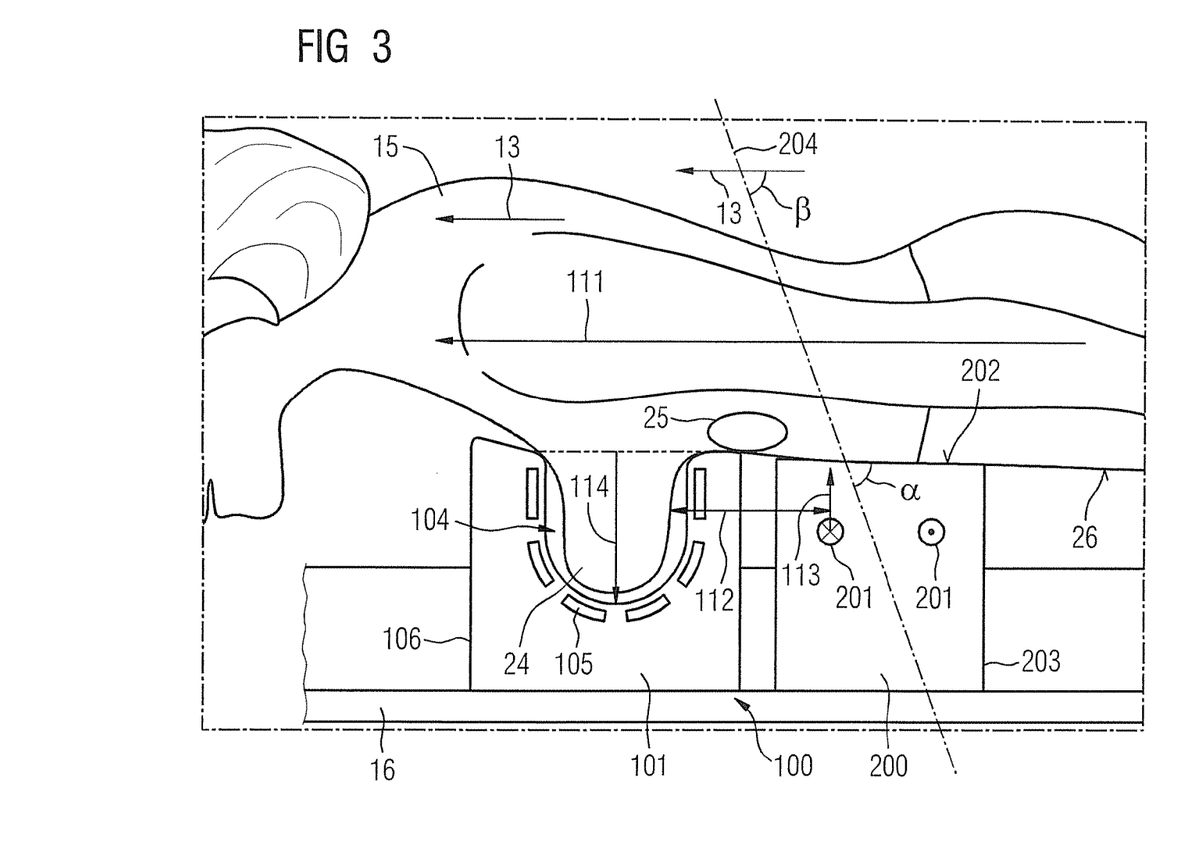
FIG. 3 schematically illustrates a magnetic resonance coil system in an alternative embodiment of the shim coil device in a state positioned on the patient.

An alternative exemplary embodiment of a shim coil device 200 is shown in FIG. 3. Substantially like components, features and functions are labeled consistently with the same reference numerals. The following description is restricted itself essentially to the differences compared to the exemplary embodiment in FIG. 2, reference being made to that description of the exemplary embodiment in FIG. 2 with regard to like components, features and functions.

The shim coil device 200 in FIG. 3 has a shim coil element 201 that is arranged inclined at an angle inside the shim coil device 200 in relation to a contact surface 202 of a housing unit 203 of the shim coil device 200. As a result, a shim coil axis 204 of the shim coil element 201 also has an angle of inclination α to the contact surface 202 and/or to a patient surface 26 of the patient 15, where α is ≥45° and α is ≤135°. In this case the shim coil axis 204 has an angle of inclination α to the contact surface 202 and/or to the patient surface 26 of the patient 15, where a is ≥35° and α is ≤125°. More advantageously, the shim coil axis 204 in this case has an angle of inclination α to the contact surface 202 and/or to the patient surface 26 of the patient 15, where a is ≥25° and α is ≤115°, and preferably the shim coil axis 204 in this case has an angle of inclination α to the contact surface 202 and/or to the patient surface 26 of the patient 15, where a is ≥15° and α is ≤105°.

Accordingly, the shim coil axis 204 of the shim coil element 201 has an angle of inclination β to the basic magnetic field direction 13, where β is ≥45° and β is ≤135°. In this case the shim coil axis 204 preferably has an angle of inclination β to the basic magnetic field direction 13, where β is ≥35° and β is ≤125°. More advantageously, the shim coil axis 204 has in this case an angle of inclination β to the basic magnetic field direction 13, where β is ≥25° and β is ≤115°, and preferably the shim coil axis 204 has in this case an angle of inclination β to the basic magnetic field direction 13, where β is ≥15° and β is ≤105°.

For a further embodiment of the shim coil device 200, reference is made to the explanation in relation to FIG. 2. Thus, the shim coil element 201 may be embodied as a circular shape (FIG. 5), an oval shape (FIG. 8), a rectangular shape (FIG. 6), or in a square shape or in a spiral shape.

An arrangement and/or position of the shim coil device 200 with respect to the local breast coil device 101 and/or to the patient support device 16 and/or to the patient 15 also corresponds to the explanation in relation to FIG. 2, so a mode of operation of the shim coil device 200 shown in FIG. 3 also corresponds to a mode of operation of the shim coil device 102 shown in FIG. 1. With regard to the arrangement of the shim coil device 200 inside the magnetic resonance coil system 100, reference is likewise made to the explanation in relation to FIG. 2.

Figure 4:
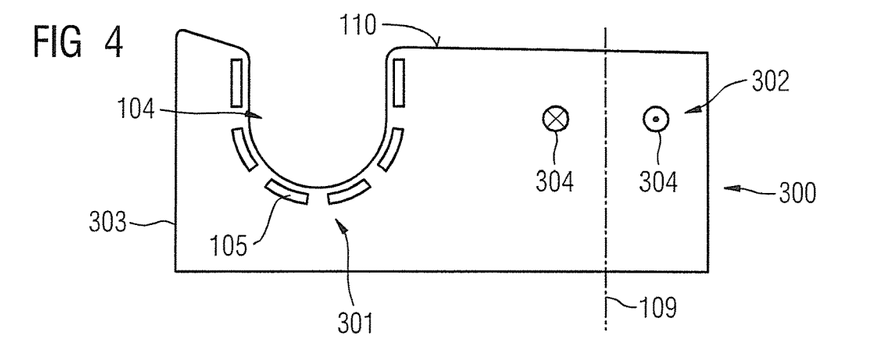
FIG. 4 schematically illustrates a further exemplary embodiment of the magnetic resonance coil system.

An alternative exemplary embodiment of a magnetic resonance coil system 300 is shown in FIG. 4. Substantially like components, features and functions are labeled consistently with the same reference numerals. The following description is restricted essentially to the differences compared to the exemplary embodiment in FIGS. 2 and 3, reference being made to the description of the exemplary embodiment in FIGS. 2 and 3 with regard to like components, features and functions.

The magnetic resonance coil system 300 in FIG. 4 has a local breast coil device 301 and a shim coil device 302. The shim coil device 302 is integrated within the local breast coil device 301. In this arrangement the local breast coil device 301 and the shim coil device 302 form a common structural unit having a single housing unit 303 which encloses both the local breast coil device 301 and the shim coil device 302.

In the shown exemplary embodiment, the shim coil device 302 is arranged inside the magnetic resonance coil system 300 toward the feet end with respect to the local breast coil device 301. In principle, a different arrangement, in particular an arrangement of the shim coil device 302 inside the magnetic resonance coil system 300 toward the head end with respect to the local breast coil device 301 is also possible.

For a further embodiment of the shim coil device 302, reference is made to the explanation in relation to FIG. 2. In particular for an embodiment of a shim coil element 304 and the arrangement and/or position of the same with respect to the housing 303 and/or the patient support device 16 and/or the patient 15 and/or the basic magnetic field direction 13, reference is made to the explanation in relation to FIGS. 2 and 3.

Figure 9:
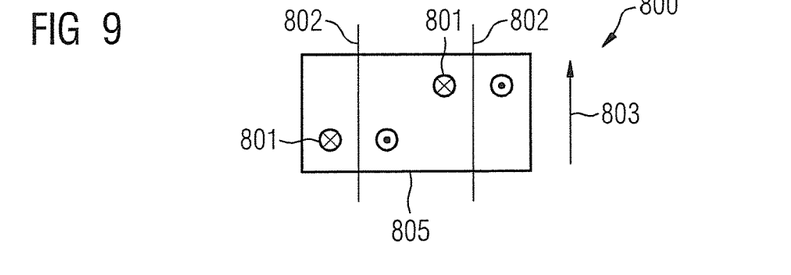
FIG. 9 schematically illustrates a further alternative exemplary embodiment of a shim coil device.

Further alternative exemplary embodiments of a shim coil device 400, 500, 600, 700, 800 are shown in FIGS. 5 and 9. Substantially like components, features and functions are labeled with the same reference numerals. The following description is restricted itself essentially to the differences compared to the exemplary embodiment in FIGS. 2 to 4, reference being made to the description of the exemplary embodiment in FIGS. 2 to 4 with regard to like components, features and functions.

FIG. 5 shows a section through the shim coil device 400 in a view from above. The shim coil device 400 has a single shim coil element 401 having a single shim coil axis 402. The shim coil element 401 is embodied with a circular shape.

Figure 6:
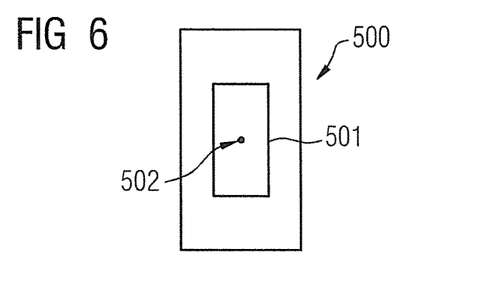
FIG. 6 schematically illustrates a further alternative exemplary embodiment of a shim coil device.

FIG. 6 shows a section through the shim coil device 500 in a view from above. The shim coil device 500 has a single shim coil element 501 having a single shim coil axis 502. The shim coil element 501 is embodied with a rectangular shape.

Figure 7:
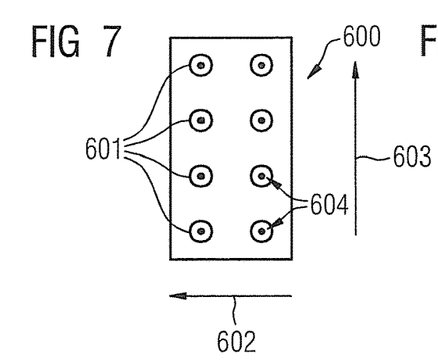
FIG. 7 schematically illustrates a further alternative exemplary embodiment of a shim coil device.

FIG. 7 shows a section through the shim coil device 600 in a view from above. The shim coil device 600 has multiple shim coil elements 601, eight shim coil elements 601 being contained in the present exemplary embodiment. The individual shim coil elements 601 are arranged in a 2×4 shim coil array. Along a direction 602 running parallel to a longitudinal extent of the patient 15 and/or of the patient support device 16 in a state of the shim coil device 600 arranged on the patient 15, a number of sequentially arranged shim coil elements 601 amounts to two coil elements 601. Along a direction 603 running perpendicularly to the longitudinal extent of the patient 15 and/or of the patient support device 16 in a state of the shim coil device 600 arranged on the patient 15, a number of sequentially arranged shim coil elements 601 amounts to four coil elements 601.

The individual coil elements 601 are embodied with a circular shape. Furthermore, the individual shim coil elements 601 each have a shim coil axis 604.

Figure 8:
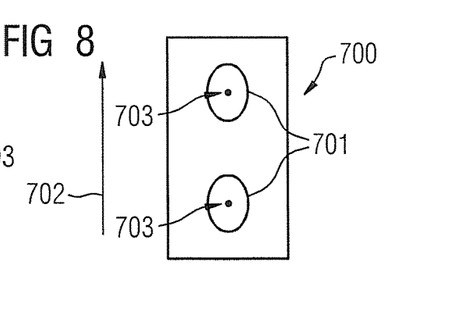
FIG. 8 schematically illustrates a further alternative exemplary embodiment of a shim coil device.

FIG. 8 shows a section through the shim coil device 700 in a view from above. The shim coil device 700 has multiple shim coil elements 701, two shim coil elements 701 being contained in the present exemplary embodiment. Along a direction 702 running perpendicularly to a longitudinal extent of the patient 15 and/or of the patient support device 16 in a state of the shim coil device 700 arranged on the patient 15, the two coil elements 701 are arranged in sequence.

The individual coil elements 701 are embodied with an oval shape. Furthermore, the individual shim coil elements 701 each have a shim coil axis 703.

FIG. 9 shows a section through the shim coil device 800, the section extending along a direction 803 of a distance from the shim coil device 800 to the patient 15. The shim coil device 800 has multiple shim coil elements 801, two shim coil elements 801 being contained in the present exemplary embodiment. The individual shim coil elements 801 each have a shim coil axis 802.

In the direction 803, the two coil elements 801 are situated offset with respect to one another, such that the two coil elements 801 are at a different distance from a housing unit 804, in particular a contact surface 805, and consequently from the patient 15.

The exemplary embodiments shown in FIGS. 5 to 9 are intended to only show examples among possible embodiment variants of the shim coil device 400, 500, 600, 700, 800. The individual shim coil devices 400, 500, 600, 700, 800 are in this case not limited to the depicted numbers of shim coil elements 401, 501, 601, 701, 801, and a different number of shim coil elements 401, 501, 601, 701, 801 inside the shim coil device 400, 500, 600, 700, 800 is possible at any time. Furthermore, a shape of the individual shim coil elements 401, 501, 601, 701, 801 shown is also not limited to the illustrated examples, and further embodiments deemed beneficial by those skilled in the art are possible.

For a further embodiment of the shim coil devices 400, 500, 600, 700, 800 shown in FIGS. 5 to 9, reference is made to the explanatory remarks given in relation to FIGS. 2 to 4. An arrangement and/or position of the shim coil devices 400, 500, 600, 700, 800 with respect to a local breast shim coil device 101, 301 and/or to the patient support device 16 and/or to the patient 16 and/or to the basic magnetic field direction β also corresponds to the explanation in relation to FIGS. 2 to 4. With regard to the arrangement of the shim coil devices 400, 500, 600, 700, 800 inside the magnetic resonance coil system 100, 300, reference is likewise made to the explanation in relation to FIGS. 2 to 4.

The shim coil devices 400, 500, 600, 700, 800 shown in FIGS. 5 to 9 are driven by the operating controller 116. In this case the individual shim coil elements 401, 501, 601, 701, 801 can be driven individually, independently of one another, by the operating controller 116.

Although modifications and changes may be suggested by those skilled in the art, it is the intention of the inventors to embody within the patent warranted hereon all changes and modifications as reasonably and properly come within the scope of their contribution to the art.

We claim as our invention:

1. A magnetic resonance (MR) coil system, comprising:
   a local breast coil device comprising a local MR coil configured to obtain MR data from a breast of a patient in an MR imaging procedure;
   a shim coil device comprising a housing having a contact surface adapted for placement beneath a prone patient in said MR scanner in which a homogenous basic magnetic field is produced that proceeds along a longitudinal direction of the patient, so that the contact surface bears against a patient surface of the patient adjacent to a breast of the patient, the patient comprising a body region next to the heart in which said basic magnetic field exhibits inhomogeneity;
   said shim coil device comprising a plurality of shim coil elements situated in said housing so as to be adjacent to but not surround said breast, said shim coil elements being situated in said housing so that, when said contact surface bears against said patient surface, said plurality of shim coil elements proceed sequentially in a direction along the longitudinal direction of the patient;
   said shim coil elements being configured to produce a compensating magnetic field having field lines in an orientation in which said field lines proceed relative to said basic magnetic field in said body region so as to compensate said inhomogeneity of said basic magnetic field in said body region during said MR imaging procedure of the breast, and in which said field lines proceed in said breast relative to said basic magnetic field so as to not alter said basic magnetic field in said breast during said procedure;
   each shim coil element forming a plane that is situated at a distance beneath said contact surface and said patient surface, said plane having a center and each shim coil element having a shim coil axis that proceeds through said center perpendicular to said plane, with said shim coil axis oriented with an angle of inclination α relative to at least one of said contact surface and said patient surface, with 45°≤α≤135°, so as to produce said orientation of said field lines of said compensating magnetic field; and
   said local breast coil device and said shim coil device being situated in a sequence along said longitudinal direction of the patient.

2. A magnetic resonance coil system as claimed in claim 1 wherein said local breast coil device comprises a breast coil device housing, and wherein said housing of said shim coil device is integrated within said breast coil device housing.

3. A magnetic resonance coil system as claimed in claim 1 wherein said local breast coil device comprises a breast coil receiving zone having a depth, and wherein said shim coil elements situated in said housing of said shim coil device at a distance from said contact surface that is half of said depth.

4. A shim coil device comprising:
   a housing having a contact surface adapted for placement beneath a prone patient in a magnetic resonance (MR) scanner in which a homogenous basic magnetic field is produced that proceeds along a longitudinal direction of the patient, so that the contact surface bears against a patient surface of the patient adjacent to a breast of the patient, the patient comprising a body region next to the breast in which said basic magnetic field exhibits inhomogeneity;
   a plurality of shim coil elements in said housing so as to be adjacent to but not surround said breast, said shim coil elements being situated in said housing so that, when said contact surface bears against said patient surface, said plurality of shim coil elements proceed sequentially in a direction along the longitudinal direction of the patient;
   said shim coil elements being configured to produce a compensating magnetic field having field lines in an orientation in which said field lines proceed relative to said basic magnetic field in said body region so as to compensate said inhomogeneity in said basic magnetic field in said body region during an MR imaging procedure of the breast, and in which said field lines proceed in said breast relative to said basic magnetic field so as to not alter said basic magnetic field in said breast during said procedure; and
   each shim coil element forming a plane that is situated at a distance beneath said contact surface and said patient surface, said plane having a center and each shim coil element having a shim coil axis that proceeds through said center perpendicular to said plane, with said shim coil axis oriented with an angle of inclination α relative to at least one of said contact surface and said patient surface, with 45°≤α≤135°, so as to produce said orientation of said field lines of said compensating magnetic field.

5. A shim coil device as claimed in claim 4 wherein said housing comprises a receptacle, adjacent to said shim coil elements, having a shape adapted to receive said breast therein when said patient is in said prone position in said MR scanner.

6. A shim coil device as claimed in claim 4 wherein α is 90°.

7. A shim coil device as claimed in claim 4 wherein, when said contact surface bears against said patient surface, each shim coil axis has an angle of inclination β with respect to said direction of said basic magnetic field, with 45°≤β≤135°.

8. A shim coil device as claimed in claim 7 wherein β is 90°.

9. A shim coil device as claimed in claim 4 wherein said housing is configured to place said shim coil elements relative to said body region so that said body region and said shim coil elements overlap a maximum of 50% of said body region.

10. A shim coil device as claimed in claim 4 wherein each shim coil element has a shape selected from the group consisting of a circular shape, an oval shape, a rectangular shape, a square shape, and a spiral shape.

11. A shim coil device as claimed in claim 4 wherein each shim coil element is situated in said housing at a distance in a range between 0 cm to 2 cm from said contact surface.

12. A shim coil device as claimed in claim 4 comprising an operating controller configured to supply current to the respective shim coil elements individually.

* * * * *